(12) United States Patent
Brockway et al.

(10) Patent No.: US 7,347,822 B2
(45) Date of Patent: Mar. 25, 2008

(54) PRESSURE MEASUREMENT DEVICE (75) Inventors: Brian P. Brockway, Arden Hills, MN (US); Perry Alton Mills, Arden Hills, MN (US); Mel Murray Moench, Howard Lake, MN (US)

(73) Assignee: Transoma Medical, Inc., St. Paul, MN (US)

( * ) Notice: Subject to any disclaimer, the term of this patent is extended or adjusted under 35 U.S.C. 154(b) by 0 days.

(21) Appl. No.: 11/304,452

(22) Filed: Dec. 14, 2005

(65) Prior Publication Data

US 2006/0094966 A1 May 4, 2006

Related U.S. Application Data

(60) Continuation of application No. 09/997,850, filed on Nov. 29, 2001, now Pat. No. 7,025,727, which is a continuation of application No. 09/491,233, filed on Jan. 25, 2000, now Pat. No. 6,379,308, which is a division of application No. 08/950,315, filed on Oct. 14, 1997, now Pat. No. 6,033,366.

(51) Int. Cl.
*A61B 5/00* (2006.01)

(52) U.S. Cl. ...................... 600/486; 600/485
(58) Field of Classification Search ............ None
See application file for complete search history.

(56) References Cited

U.S. PATENT DOCUMENTS

| | | |
|---|---|---|
| 3,550,583 A | 12/1970 | Chiku et al. |
| 3,865,100 A | 2/1975 | Kanai et al. |
| 3,867,950 A | 2/1975 | Fischell |
| 3,893,451 A | 7/1975 | Durand et al. |

(Continued)

FOREIGN PATENT DOCUMENTS

DE 19644856 5/1997

(Continued)

OTHER PUBLICATIONS

Brockway et al., "A New Method for Continuous Chronic Measurement and Recording of Blood Pressure, Heart Rate and Activity in the Rat Via Radio-Telemetry," *Clinical and Experimental Hypertension—Theory and Practice*, A13(5):885-895 (1991).

(Continued)

*Primary Examiner*—Robert L. Nasser
(74) *Attorney, Agent, or Firm*—Fish & Richardson P.C.

(57) ABSTRACT

A device measures pressures in animals and humans and includes a pressure transmission catheter (PTC) filled with a pressure transmitting medium and implantable in an area in having a physiological pressure. A transducer communicates with the pressure transmitting medium to provide a pressure signal representing variations in the physiologic pressure on electrical wires. A connecting catheter carries the electrical wires to signal processing and telemetry circuitry, which transmits a telemetry signal representing the pressure signal to a receiver external to the animal or human. A housing holds the signal processing and telemetry circuitry, but the transducer is remote from the housing. The device is particularly useful in measuring venous pressure, pulmonary pressure, bladder pressure, or intracranial pressure without significant head pressure artifact and with a sufficient dynamic response. One embodiment of the PTC includes a multi-durometer stem.

4 Claims, 7 Drawing Sheets

U.S. PATENT DOCUMENTS

| | | | |
|---|---|---|---|
| 3,942,382 A | 3/1976 | Hok | |
| 3,958,558 A | 5/1976 | Dunphy et al. | |
| 4,160,448 A * | 7/1979 | Jackson | 600/486 |
| 4,207,903 A | 6/1980 | O'Neill | |
| RE30,366 E | 8/1980 | Rasor et al. | |
| 4,325,387 A | 4/1982 | Helfer | |
| 4,385,636 A | 5/1983 | Cosman | |
| 4,407,296 A | 10/1983 | Anderson et al. | |
| 4,483,196 A | 11/1984 | Kurtz et al. | |
| 4,485,813 A | 12/1984 | Anderson et al. | |
| 4,494,950 A | 1/1985 | Fischell | |
| 4,519,401 A | 5/1985 | Ko et al. | |
| 4,557,269 A | 12/1985 | Reynolds et al. | |
| 4,576,181 A | 3/1986 | Wallace et al. | |
| 4,596,563 A | 6/1986 | Pande | |
| 4,610,256 A | 9/1986 | Wallace | |
| 4,718,425 A | 1/1988 | Tanaka et al. | |
| 4,741,345 A | 5/1988 | Matthews et al. | |
| 4,796,641 A | 1/1989 | Mills et al. | |
| 4,834,710 A | 5/1989 | Fleck | |
| 4,846,191 A | 7/1989 | Brockway et al. | |
| 4,899,752 A | 2/1990 | Cohen | |
| 4,913,147 A | 4/1990 | Fahlstrom et al. | |
| 4,987,897 A | 1/1991 | Funke | |
| 5,129,394 A | 7/1992 | Mehra | |
| 5,192,314 A | 3/1993 | Daskalakis | |
| 5,199,427 A | 4/1993 | Strickland | |
| 5,217,439 A | 6/1993 | McClusky | |
| 5,218,957 A | 6/1993 | Strickland | |
| 5,242,399 A | 9/1993 | Lau et al. | |
| 5,348,536 A | 9/1994 | Young et al. | |
| 5,353,800 A | 10/1994 | Pohndorf et al. | |
| 5,373,852 A | 12/1994 | Harrison et al. | |
| 5,411,551 A | 5/1995 | Winston et al. | |
| 5,431,171 A | 7/1995 | Harrison et al. | |
| 5,450,853 A | 9/1995 | Hastings et al. | |
| 5,487,760 A | 1/1996 | Villafana | |
| 5,498,251 A | 3/1996 | Dalton | |
| 5,535,752 A | 7/1996 | Halperin et al. | |
| 5,538,005 A | 7/1996 | Harrison et al. | |
| 5,545,151 A | 8/1996 | O'Connor et al. | |
| 5,551,427 A | 9/1996 | Altman | |
| 5,593,430 A | 1/1997 | Renger | |
| 5,702,427 A | 12/1997 | Ecker et al. | |
| 5,796,827 A | 8/1998 | Coppersmith et al. | |
| 5,807,265 A | 9/1998 | Itoigawa et al. | |
| 5,895,374 A | 4/1999 | Rodstein | |
| 5,899,927 A | 5/1999 | Ecker et al. | |
| 6,015,387 A | 1/2000 | Schwartz et al. | |
| 6,019,728 A | 2/2000 | Iwata et al. | |
| 6,019,729 A | 2/2000 | Itoigawa et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feirbach | |
| 6,159,156 A | 12/2000 | Van Bockel | |
| 6,193,670 B1 | 2/2001 | Van Tassel et al. | |
| 6,296,615 B1 | 10/2001 | Brockway et al. | |
| 6,379,308 B1 | 4/2002 | Brockway | |
| 6,659,959 B2 | 12/2003 | Brockway et al. | |
| 2003/0195428 A1 | 10/2003 | Brockway et al. | |

FOREIGN PATENT DOCUMENTS

| | | |
|---|---|---|
| EP | 337 035 | 10/1989 |
| EP | 482 487 | 4/1992 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |

OTHER PUBLICATIONS

Meindl et al., "Implantable Telemetry in Biomedical Research," *IEEE Trans. Biomed. Engineering, BME*, 31(12):817-823 (1984).

Sato et al., "Evaluation of a New Method Using Telemetry for Monitoring the Left VEntricular Pressure in Free-Moving Rats," *J. Pharm. & Tox. Methods*, 31(4):191-198 (1994).

Van Den Buuse, M., "Circadian Rhythms of Blood Pressure, Heart Rate, and Locomotor Activity in Spontaneously Hypertensive Rats as Measured with Radio-Telemetry," *Phys. & Behavior*, 55(4):783-787 (1994).

Zimmerman, T. G., "Personal Area Networks: Near-field intrabody communication," *IBM Systems Journal* (USA), 35(3-4):609-617 (1996).

* cited by examiner

PRESSURE MEASUREMENT DEVICE

CROSS-REFERENCE TO RELATED APPLICATIONS

This application is a continuation of co-pending U.S. application Ser. No. 09/997,850, filed Nov. 29, 2001, which is a continuation U.S. Pat. No. 6,379,308, Issued Apr. 30, 2002, which is a divisional of U.S. Pat. No. 6,033,366, Issued Mar. 7, 2000, the specifications of which are incorporated herein by reference.

STATEMENT REGARDING FEDERALLY SPONSORED RESEARCH OR DEVELOPMENT

Portions of this invention were developed under Contract No. 2 R44 HL55823-02, awarded by the National Institutes of Health. Therefore, the U.S. Government may have a paid-up license in portions of this invention and the right, in limited circumstances, to require the patent owner to license others on reasonable terms as provided for by the terms of the contract.

THE FIELD OF THE INVENTION

The present invention relates generally to implantable devices, and in particular to implantable devices for measuring various physiological pressures in humans or animals, such as blood pressure, intracranial pressure, bladder pressure, and pulmonary pressure.

BACKGROUND OF THE INVENTION

Measurement of physiological pressures is of interest to both clinicians and researchers. Physiological pressure measurements obtained from laboratory animals provide researchers with valuable information regarding the safety and efficiency of pharmaceutical agents, and the toxicity of chemicals, and leads to better understanding of human physiology. Physiological pressure measurements also have human clinical values, such as providing diagnostic information, assessing the safety and efficiency of drugs in clinical trials, and controlling implantable medical devices, such as pacemakers.

Arterial blood pressure is of particular interest to the researcher or clinician, because arterial blood pressure fluctuates over time in response to various conditions, such as an injection of pharmaceutical agent or chemical, or the activity level of an animal being observed. Arterial blood pressure fluctuations, however, often make it necessary to obtain chronic, frequent measurements to identify the effect of the injected pharmaceutical agent or chemical, or to properly control an implantable medical device.

In addition to arterial blood pressure, other pressure measurements are also of interest, such as venous pressure, pulmonary pressure, intracranial pressure, bladder pressure, intrauterine pressure, gastrointestinal pressure, and other physiological pressures. For example, intrapleural or blood pressure can be used to determine the rate of respiration in addition to providing general information related to respiratory function. Measurements of intracranial pressure from laboratory animals are often used to project which methods of treatment and management are most effective in humans.

Chronic measurement of physiological pressures provides vital information for clinical care of humans. Patients with high blood pressure could benefit from an implantable device which could chronically monitor pressure as a means of determining optimal dosage for a drug or biofeedback therapy. Such a device could also be used as a means of providing feedback to a closed-loop drug delivery system for controlling blood pressure, or to a cardiac pacemaker as a means of optimizing pacing control parameters.

Infants who have been identified as being at risk for sudden infant death syndrome could also benefit. It is desirable to monitor changes in intrapleural pressure as a reliable measurement of respiratory rate in these infants by means which would allow the infant to roll and move freely about its crib without being restrained by wires extending from a vest.

Chronic monitoring of intracranial pressure is also important for infants with hydrocephalitis and patients with head injury. Hydrocephalitis and head injuries can cause excessive pressure buildup within the brain, resulting in death or serious brain damage. In most cases, corrective action can be taken if the buildup of pressure can be quickly detected.

This need to obtain accurate and ongoing physiological pressure measurements within various parts of animals and humans is discussed in detail in the Brockway U.S. Pat. No. 4,846,191 assigned the assignee of the present application, and which is herein incorporated by reference. The Brockway et al. '191 patent discloses a pressure measurement device for monitoring physiological pressures, such as blood pressure, in various locations in an animal or human. The pressure measurement device utilizes a fluid-filled pressure transmission catheter (PTC) with a gel membrane located at a tip of the PTC. The tip of the PTC is positioned in an area where physiological pressure is to be measured. The PTC extends from a small implantable housing that contains a transducer, signal-processing and telemetry circuitry, and a battery. The fluid-filled PTC communicates the pressure from the area where pressure is to be measured to the transducer within the housing, which generates an electrical pressure signal representing the communicated pressure. The signal-processing and telemetry circuitry in the housing receives the pressure signal generated by the transducer and provides a telemetry signal representing the pressure signal. The signal-processing and telemetry circuitry transmits the telemetry signal to a receiver which is external to the animal or human.

In some applications of the pressure measurement device disclosed in the Brockway et al. '191 patent, the housing cannot be implanted within close proximity to the area where pressure is to be measured due to physical limitations and practical considerations of surgical procedures. When the housing is not within close proximity to the area where pressure is to be measured, the length of the catheter that is required may be too long to assure that errors, resulting from decreased dynamic response or changes in posture, be within acceptable limits for the given application. For example, if the vertical distance from the PTC tip to the transducer changes due to posture, an error in the pressure measurement occurs. Every one centimeter change in vertical distance creates approximately one millimeter Hg error in the pressure measurement for one preferred low-viscosity fluid used in the catheter. This pressure measurement error is known as "head pressure artifact" and is very significant in certain applications. Furthermore, as the length of the PTC increases, the dynamic response of the pressure measurement device is reduced. In certain applications, the required length of the PTC is so long that a sufficient dynamic response cannot be obtained.

In addition, the Brockway et al. '191 patent does not disclose a pre-compensated, disposable, and easily replaceable transducer. Rather, since the transducer is inside the housing, if the transducer disclosed in the Brockway et al. '191 patent fails, the entire pressure-sensing device must be returned to the manufacturer for replacement to ensure proper compensation, mounting of the transducer, and sealing of the implant body.

For reasons stated above and for other reasons presented in greater detail in the Description of the Preferred Embodiments section of the present specification, there is a need for a pressure measurement device that is capable of measuring pressures in more animal and human applications, with better dynamic response, and with more accurate pressure measurements than currently possible with present pressure measurement devices. In addition, it is desired that the transducer and catheter of the pressure measurement device be more easily replaceable than currently possible with present pressure measurement devices.

SUMMARY OF THE INVENTION

The present invention provides a pressure measurement device which measures physiological pressures in animals and humans. The pressure measurement device includes a pressure transmission catheter filled with a pressure transmitting medium and implantable in an area having a physiological pressure. A transducer is in communication with the pressure transmitting medium to provide a pressure signal representing variations in the physiologic pressure on electrical wires. A connecting catheter carries the electrical wires to signal processing and telemetry circuitry, which receives the pressure signal and provides a telemetry signal representing the pressure signal. A housing holds the signal processing and telemetry circuitry. The transducer is remote from the housing.

The pressure transmission catheter preferably has a length short enough to avoid significant head pressure artifact and to provide sufficient dynamic response, but long enough to accommodate surgical limitations and tolerance concerns. For example, depending on the particular application of the pressure measurement device, the pressure transmission catheter typically has a length somewhere in the range from approximately five millimeters to approximately four centimeters. In most applications, the pressure transmitting medium comprises a gel and a liquid. Nevertheless, because the present invention permits the pressure transmission catheter to be significantly shorter than previously possible, in certain applications, the pressure transmitting medium includes only a gel. In one embodiment, the transducer is integral with the pressure measurement catheter to form a transducer-tipped catheter.

The pressure measurement device according to the present invention can be employed to accurately measure low pressure where head pressure artifact can constitute a significant percentage of the pressure being measured. These pressures include: venous pressure; pulmonary pressure; intracranial pressure; bladder pressure; and other pressures. The pressure measurement device measures these pressures without significant head pressure artifact and with a sufficient dynamic response.

The transducer is preferably pre-temperature compensated and disposable. In this way, the transducer, which is external to the housing, can be easily replaced without replacing the entire pressure measurement device. In many applications of the pressure measurement device, the housing is implantable remote from the area having the physiological pressure.

In one form of the invention, the pressure transmitting catheter includes a lumen filled with the pressure transmitting medium. An inner layer material surrounds the lumen and an outer layer material surrounds the inner layer material. The outer layer material is of a different hardness than the inner layer material. In a preferred embodiment, the inner layer material is harder then the outer layer material. Preferably, the harder layer material essentially determines the frequency response of the pressure transmitting catheter so that compared to a catheter fabricated of only softer material, the catheter of the present invention provides improved frequency response. Preferably, the softer layer material makes the pressure transmitting catheter more flexible and kink resistant compared to a catheter fabricated of only harder material. A transition between the inner layer material and the outer layer material can be a sharp transition or a gradient transition. In one embodiment, the inner layer material comprises 72 D urethane and the outer layer material comprises 80 A urethane.

The pressure measurement device according to the present invention achieves more accurate measurement of physiological pressure and can be employed in many new applications for pressure measurement in animals and humans. The pressure measurement device according to the present invention obtains high-fidelity measurements with negligible head pressure error in applications where the distance from the distal tip of the pressure transmission catheter to the transmitter is such that significant head pressure errors could occur with conventional devices.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
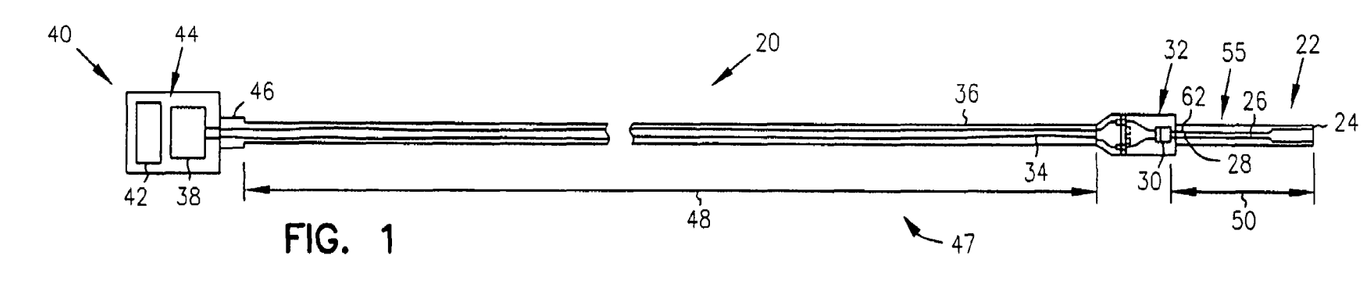
FIG. 1 is a diagram of a pressure measurement device according to the present invention.

A pressure measurement device according to the present invention is illustrated generally at 20 in FIG. 1. Pressure measurement device 20 is a miniature implantable device capable of measuring internal physiological body pressure in humans or animals. The fundamental principles by which pressure measurement device 20 measures pressure are described in detail in the Brockway et al. '191 patent, which was incorporated by reference in the Background of the Invention section of the present specification. Therefore, for clarity, many of the features of pressure measurement device 20 which are similar to the pressure measurement device described in the Brockway et al. '191 patent are not discussed herein. However, the features which differ from the pressure measurement device described in the Brockway et al. '191 patent are discussed in detail below.

Pressure measurement device 20 includes a pressure transmission catheter (PTC) 22 having a distal lumen tip 24 which is positioned within the body of a human or animal at the site where pressure is to be measured. One embodiment of PTC 22 is flexible, while another embodiment of PTC 22 is rigid, and the particular embodiment of PTC 22 selected depends on the given application of pressure measurement device 20. PTC 22 is filled with a pressure-transmitting medium 26 which communicates the pressure at the distal tip 24 of PTC 22 to a proximal lumen end 28 of PTC 22. Thus, a portion of pressure-transmitting medium 26 at distal tip 24 interfaces with the substance in the body area where. pressure is to be measured, such as with blood in an artery.

A transducer 30 is in communication with pressure-transmitting medium 26 at the proximal end 28 of PTC 22. Transducer 30 is contained in a transducer housing 32. Transducer 30 responds to variations in the pressure-transmitting medium at proximal end 28 to provide an electrical pressure signal representing variations in the physiological pressure at distal. tip 24 on electrical lead wires 34. Electrical leads wires 34 are carried within a connecting catheter 36. By separating PTC 22 from connecting catheter 36, the length of connecting catheter 36, indicated by arrows 48, can be independently determined from the length of PTC 22, indicated by arrows 50. The length of connecting catheter 36, indicated by arrows 48, varies from zero to very long, depending on the application of pressure measurement device 20.

Electrical lead wires 34 are coupled to an electronics module 38 of a transmitter 40. Electronics module 38 is powered by a battery 42. Battery 42 and electronics module 38 are contained within a transmitter housing 44. The electronics module 38 includes signal-processing and telemetry circuitry and a transmitting antenna for generating and transmitting a telemetry signal representing the pressure signal from transducer 30 to an external receiver (not shown) disposed outside of the human or animal. The electrical pressure signal produced by transducer 30 is amplified and filtered with the signal-processing circuitry in electronics module 38 and is then modulated onto a radio-frequency carrier by the telemetry circuitry in electronics module 38 for transmission to the external receiver. A suitable telemetry system is described in the Brockway et al. '191 patent and the patent application entitled "Respiration Monitoring System Based on Sensed Blood Pressure Variations," Ser. No. 08/535,656, filed Sep. 28, 1995, assigned to the assignee of the present application, and which is herein incorporated by reference.

In one embodiment of pressure measurement device 20, connecting catheter 36 is coupled to transmitter 40 with a water-tight or non-water-tight connector 46. In this embodiment, the electrical lead wires 34 contained connecting catheter 36 interface with electronics module 38 via connector 46. Water-tight or non-water-tight connector 46 permits an assembly 47 including connecting catheter 36, transducer 30, and PTC 22 to be manufactured and sold separately from transmitter 40. Connector 46 also provides more flexibility for manufacturing assembly 47 and transmitter 40 and additional flexibility for customers in selecting lengths of connecting catheter 36 and PTC 22 independent from transmitter 40.

Figure 2A:
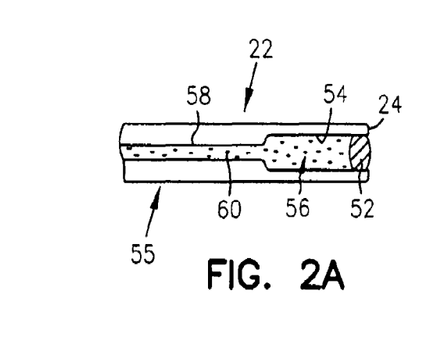
FIGS. 2A-D are slightly more detailed diagrams of various embodiments of a portion of a pressure transmission catheter (PTC) employed in the pressure measurement device of FIG. 1.

One embodiment of PTC 22 is illustrated in more detail in FIG. 2A. In this embodiment of PTC 22, a viscous gel membrane 52 is disposed at the distal tip 24 of PTC 22. A thin-walled section 54 defines an open cavity 56. A stem 55 of PTC 22 runs from the thin-walled section 54 to proximal end 28 of PTC 22, as illustrated in FIG. 1. As illustrated in FIG. 2A, the gel membrane 52 is contained in a distal portion of open cavity 56. Open cavity 56 is connected to a lumen 58 of PTC 22. The portion of open cavity 56 not filled with viscous gel 52 and lumen 58 are filled with a low-viscosity fluid 60. In this way, physiological pressure is transmitted from distal tip 24 of PTC 22 through the walls of the PTC and via viscous gel 52 contained within thin-walled section 54 to the low-viscosity fluid 60 which communicates pressure directly to transducer 30 at the proximal end 28 of lumen 58. The low frequency components of the physiological pressure are essentially transmitted via viscous gel 52 while the high frequency components of the physiological pressure are essentially transmitted through the walls of the PTC.

In one embodiment, PTC 22 is fabricated of a urethane material or other suitable biocompatible material. Viscous gel membrane 52 is a biocompatible and blood-compatible gel or other gel-like material that provides a direct interface with the tissue or fluid from which. pressure is to be measured, such as blood in an artery. Viscous gel 52 provides a means of retaining fluid within lumen 58 and is of a viscosity much higher than that of low-viscosity fluid 60. Viscous gel 52 can be comprised of any material which is capable of flowing or moving within PTC 22 as does a viscous fluid or a plug that can slide or deform easily and contains intramolecular forces which make it very unlikely that any portion of this material will dissolve, break apart, slough off, or wash away when measuring physiological pressure within a human or animal. Viscous gel 52 must be viscous enough not to wash out of PTC 22, but also must be low enough in viscosity that it can "flow" without significant pressure differential. In one embodiment of the invention, viscous gel 52 is a silicone gel which contains cross-linked molecular entities.

Low-viscosity fluid 60 preferably has a minimal biological activity (in case of failure of a seal), has a low thermal coefficient of expansion, is insoluble in gel 52, has a low specific gravity, has a negligible rate of migration through the walls of PTC 22, and has a low viscosity at body temperature. In one embodiment, low-viscosity fluid 60 is an inert perfluorocarbon.

Figure 2B:
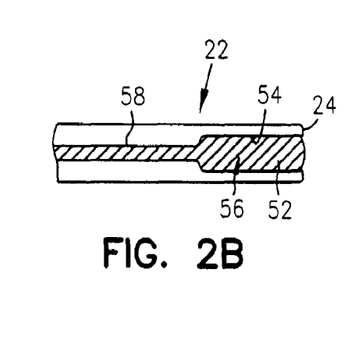

In other embodiments of the pressure measurement device according to the present invention, PTC 22, which can be rigid or flexible, is very short, and can be as short as approximately 2 mm long. One such embodiment is illustrated in FIG. 2B. In the embodiment illustrated in FIG. 2B, since the length of PTC 22 is very short, PTC 22 is typically filled entirely with viscous gel 52 (i.e, the low-viscosity fluid 60 is not used), but still provides a sufficient dynamic response.

The thin-walled section 54 reduces movement of viscous gel 52 during events that change either the volume of low-viscosity fluid 60 or the internal volume of lumen 58 of PTC 22, such as occurs during thermal expansion and contraction, bending, and hydration of the catheter material of PTC 22. Reducing the degree of displacement of gel 52 during bending of PTC 22 has the effect of reducing measurement artifact that can occur during normal movement of the human or animal into which pressure measurement device 20 is implanted. Reducing the degree of displacement of gel 52 during bending of PTC 22 reduces the amount of dead space within PTC 22 and beyond gel 52, and therefore, contributes to improved patency in blood. Thin-walled section 54 also improves the frequency response of PTC 22 by providing a means by which to transfer high-frequency components of the pressure signal into lumen 58 through the compliant thin walls of the tip.

Figure 2C:
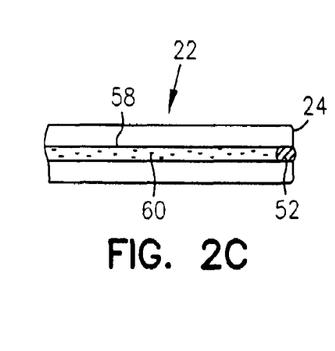
Figure 2D:
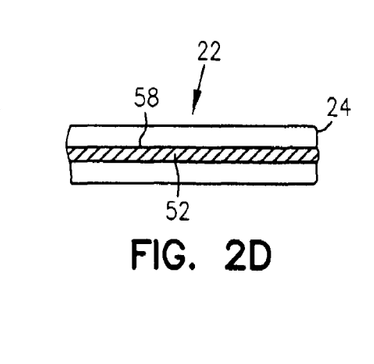

Two additional embodiments of a PTC 22 are illustrated in FIGS. 2C and 2D. In these embodiments, PTC 22 does not include an open cavity 56 defined by a thin-walled section 54, but instead, the small diameter portion of lumen 58 runs all the way to the distal tip 24. This embodiment can be used in certain applications where the above advantages of having such a thin-walled section are not as significant to obtaining satisfactory pressure measurements. In the embodiment of PTC 22 illustrated in FIG. 2C, a viscous gel membrane 52 is disposed at the distal tip 24 of PTC 22 with the remainder of lumen 58 being filled with a low-viscosity fluid 60. In the embodiment of PTC 22 illustrated in FIG. 2D, the PTC is filled entirely with viscous gel 52 (i.e., the low-viscosity fluid 60 is not used).

Figure 3:
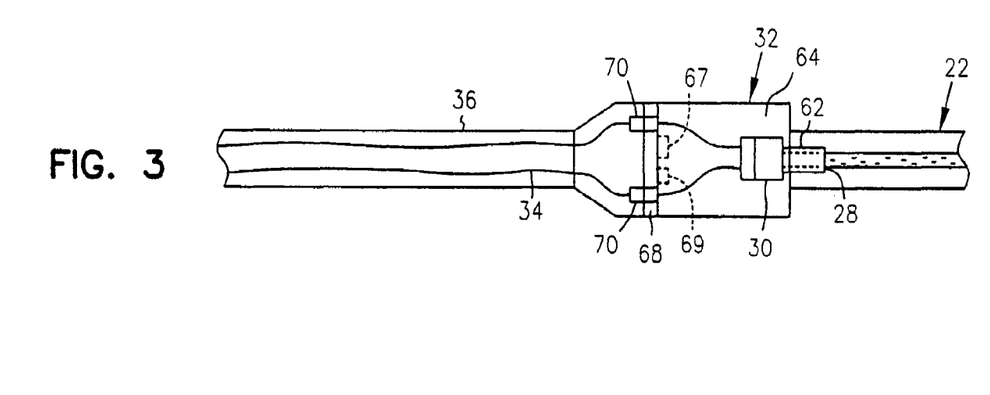
FIG. 3 is a slightly more detailed diagram of one embodiment of a transducer and the transducer's connections to the PTC and a connecting catheter employed in the pressure measurement device of FIG. 1.

A more detailed diagram of one embodiment of transducer 30 and the coupling of transducer 30 to PTC 22 and to connecting catheter 36 is illustrated in FIG. 3. As illustrated, PTC 22 is attached to transducer 30 via a nipple 62. In one embodiment of the invention, transducer housing 32 comprises a hermetic titanium housing. Transducer 30 is contained within a sealed chamber 64. Sealed chamber 64 protects transducer 30 from body fluids. Electrical connections from transducer 30 are coupled to a circuit board 68. Circuit board 68 includes circuitry 67 employed for temperature-compensating transducer 30. In an alternate embodiment, temperature of transducer 30 is measured by a sensor 69 on circuit board 68 and a remote computing device (not shown) employs these temperature measurements to temperature-compensate transducer 30. Electrical connections from circuit board 68 pass out of sealed chamber 64 via glass-metal seals 70 to thereby connect to electrical lead wires 34 contained within connecting catheter 36.

Although transducer 30 is typically smaller than the transducer employed in the pressure measurement device described in the Brockway et al. '191 patent to permit transducer 30 to be disposed remote from the transmitter housing 44, the general operation and construction of a suitable transducer 30 is described in detail in the Brockway '191 patent.

Figure 4:
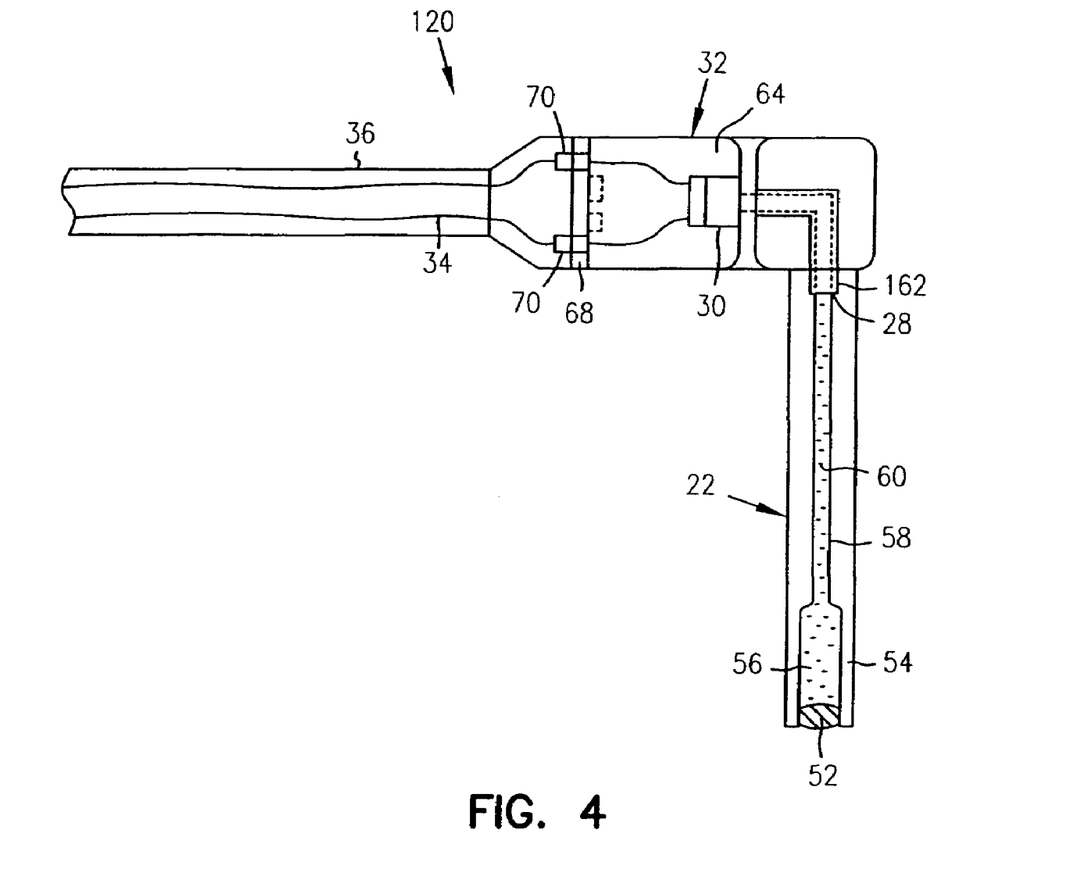
FIG. 4 is a diagram of an alternative embodiment of pressure measurement device according to the present invention.

An alternative embodiment pressure measurement device 120 is partially illustrated in FIG. 4. Pressure measurement device 120 is similar to pressure measurement device 20 illustrated in FIG. 1. However, PTC 22 couples to transducer housing 32 at a right angle in pressure measurement device 120. This is made possible with a nipple 162 which is L-shaped to receive the proximal end 28 of lumen 58 of PTC 22 to couple the low-viscosity fluid 60 to transducer 30. This right-angle embodiment is only one of many examples of the great flexibility provided by having PTC 22 separated from connecting catheter 36 and having transducer 30 being remote from transmitter housing 44.

In the preferred embodiment of the pressure measurement device described in the Brockway et al. '191 patent, a transmitter housing houses an electronics module, a battery to power the electronics module, and a transducer. For some applications, locating the transducer within the transmitter housing creates certain disadvantages to sensing accurate pressure. For example, for one preferred low-viscosity fluid 60, a head pressure error is created approximately equal to one mm Hg for every one cm of vertical distance between the tip of the PTC and the transducer. This head pressure error can be very significant relative to the pressures being measured in some applications. Another disadvantage is that the dynamic response of the PTC is inversely proportional to its length. Therefore, when the required length of the PTC becomes too long in some applications, the dynamic response is reduced to a level which is not sufficient to reproduce a high-fidelity waveform. Still another disadvantage of the preferred embodiment described in the Brockway et al. '191 patent is that for some combinations of material employed in the PTC, a greater volume of low-viscosity fluid contained in the lumen of the PTC results in a greater degree of thermal expansion and contraction, and greater degree of movement of the gel membrane. If movement of the gel membrane is too great, a void can develop within the tip of the PTC resulting in dead space thrombosis. Consequently, keeping the PTC short reduces the volume of low-viscosity fluid contained in the lumen of the PTC which contributes to improved patency in blood in some applications.

The pressure measurement device according to the present invention, such as pressure measurement device 20, overcomes all of the above disadvantages by providing a means of shortening the required length of PTC 22 in many applications. This length of PTC 22 is from the distal tip 24 to the proximal end 28 and is indicated by arrows 50. The reduced length 50 can greatly reduce head pressure error and improve the dynamic response to a degree which is acceptable to the researcher and clinician using the pressure measurement device.

A much shorter PTC is achievable because pressure measurement device 20 disposes transducer 30 remote from transmitter housing 44. In addition, pressure measurement device 20 employs a connecting catheter 36 which is separated from PTC 22 to carry the electrical leads 34 which couple the pressure signal from transducer 30 to electronics module 38 of transmitter 40. This permits the length of connecting catheter 36 and PTC 22 to be independently determined.

Head pressure error is significantly reduced as the distal tip of PTC 22 and transducer 30 can be brought much closer together in many applications. Since the dynamic response is inversely proportional to the length 50 of PTC 22, a shorter PTC 22 increases the dynamic response to permit reproduction of high-fidelity waveforms in many applications where previous pressure measurement devices, having too long of PTC, cannot reproduce high-fidelity waveforms. In addition, the volume of low-viscosity fluid 60 contained in lumen 58 of PTC 22 is reduced with the significantly shorter PTC 22 in some applications. The reduced volume results in significantly less thermal expansion and contraction and less degree of movement of viscous gel membrane 52. With less movement of gel membrane 52, voids are avoided at distal tip 24 of PTC 22 to prevent dead space thrombosis. The shorter PTC 22, therefore, reduces the volume of low-viscosity fluid 60 to thereby improve patency in blood. Moreover, as discussed above with reference to FIG. 2B, because PTC 22 can be very short in many applications, PTC 22 is alternatively completely filled with viscous gel 52 in certain applications and still performs acceptably. Since transducer housing 32 is much smaller than transmitter housing 44, it is possible to locate transducer 30 much closer to the pressure source with much less physiologic impact and better convenience from a surgical perspective.

The present invention also eliminates certain logistical problems for pressure measurement devices in the animal market. Presently, if a catheter is damaged or if a customer accidentally applies too much pressure and bursts the transducer, it is necessary to send the entire pressure measurement device back to the factory. With transducer 30 located remote from transmitter housing 44 and connected electrically to transmitter 40 via water-tight or non-water-tight connector 46 and the electrical lead wires 34 in connecting catheter 36, transducer 30 can easily be detached. In this way, pre-compensated transducers 30 can be sold to the customer as a disposable product and be attached by the customer without the need to return transmitter 40 for repair.

Multi-Durometer Catheter

As discussed above, the present invention permits a significant reduction in the required length of PTC in certain applications. Nevertheless, there are many characteristics of the fluid/gel-filled PTC which are critical in order to assure that the pressure communicated to transducer 30 is an accurate representation of the physiological pressure present at the distal tip 24 of PTC 22. In particular, if PTC 22 is not capable of transmitting high-frequency components of the physiological pressure at distal tip 24 to transducer 30, pressure information which is not transmitted causes an inaccurate representation of the physiological pressure to be produced by transducer 30.

Physical characteristics which affect the ability of PTC 22 to accurately transmit the physiological pressure include: the viscosity of the fluid within the PTC; the surface area of thin-walled section 54 that is exposed to low-viscosity fluid 60; the compliance of the walls of the PTC; the inner diameter of the PTC; and the length of the PTC. As to the viscosity of the fluid, viscosity of the fluid is dependent upon available materials and is to a large extent out of the control of the designer. As discussed above, the present application describes a pressure measurement device 20 having transducer 30 disposed between PTC 22 and transmitter 40 where connecting catheter 36 carries wires to couple the pressure signal from the transducer to the transmitter. This significantly reduces the required length of the PTC in certain applications. The inner diameter of the PTC and the compliance of the walls of the PTC are two factors that greatly affect the fidelity of the measured pressure. Once a critical inner diameter is reached, further reduction results in a rapid drop in frequency response of the PTC. The frequency response of the PTC improves as the compliance of the PTC walls is lowered (i.e., the stiffness of the walls is increased). The compliance of the walls is a function of the materials employed to fabricate the PTC, the construction of the PTC, and the thickness of the PTC walls.

In current commercially available pressure measurement devices having fluid-filled PTCs to refer pressure from a point of interest to a transducer, the outer diameter of the PTC is sufficiently large to permit the inner diameter to be sufficiently large and the PTC walls to be sufficiently thick to provide a sufficient frequency response. However, when a physiological pressure is measured in very small vessels, such as those in mice or in human coronary arteries, the required PTC outer diameter typically ranges from approximately 0.014 to 0.022 inches. In such a PTC, the inner diameter of PTC stem 55 must be very small (e.g., less than approximately 0.008 inches) and the walls of the PTC stem must be very thin (e.g., less than approximately 0.005 inches). The very small inner diameter of PTC stem 55 and the thin walls of the PTC stem result in reduced frequency response when a flexible thermoplastic is used to fabricate the PTC.

One approach to solve the frequency response problem caused by thin PTC stem walls and a very small diameter PTC stem is to fabricate PTC stem 55 of a hard material, such as 75 Shore D utethane. However, a PTC stem fabricated of this hard material is too stiff to be handled easily during surgery and kinks too easily. Another approach to improve the frequency response of a PTC stem having a very small inner diameter and thin walls is to reduce the compliance of the walls by winding a wire in a helix around the PTC stem. Nevertheless, this wire-around approach is expensive to manufacture and is very difficult to do in a reliable manner when the wall thickness of the PTC is less than 0.004 inches.

Figure 5:
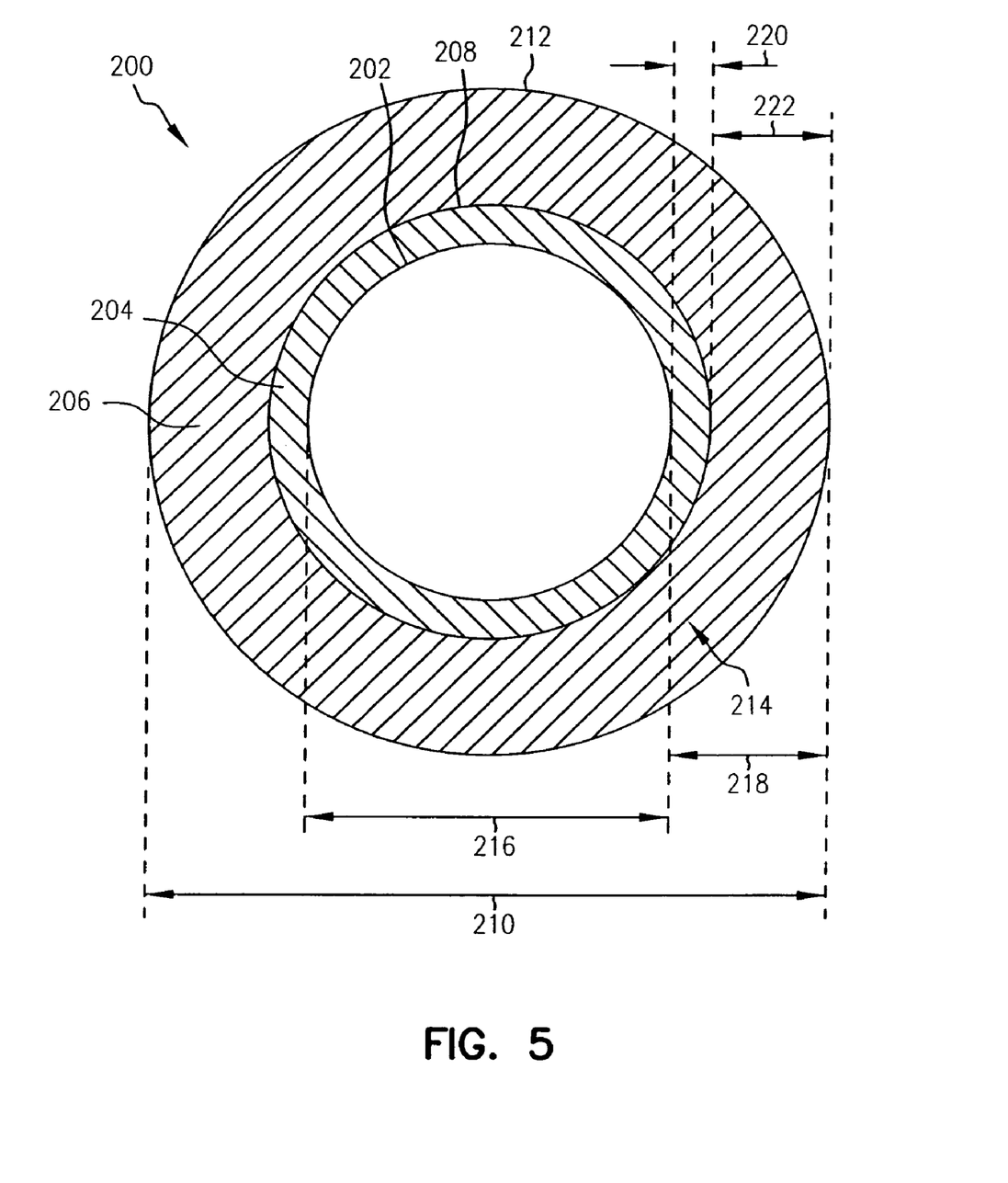
FIG. 5 is a diagram illustrating a cross-section of a multi-durometer catheter according to the present invention.

A cross-section of a multi-durometer catheter according to the present. invention is illustrated generally at 200 in FIG. 5. Multi-durometer catheter 200 forms the stem portion of a fluid-filled catheter (PTC), such as the stem 55 of PTC 22 described above. This stem portion transfers pressure from the tip of the PTC to the transducer.

Multi-durometer catheter 200 includes a lumen 202. Lumen 202 is surrounded by an inner layer of harder material 204. The inner layer of harder material 204 is surrounded by an outer layer of softer (more compliant) material 206. The transition between the inner layer of harder material 204 and the outer layer of softer material 206 is defined by an interface 208. The interface 208 can be a gradient interface to gradually transition from the inner layer to the outer layer or can alternatively be a sharp transition interface between the inner layer and the outer layer.

Multi-durometer catheter 200 has an outer diameter indicated by arrows 210 and defined by an outer surface 212. The outer diameter indicated by arrows 210 is typically in the range from approximately 0.014 to 0.022 inches. A wall 214 of catheter 200 is formed by the inner layer of harder material 204 and the outer layer of softer material 206. With the outer catheter diameter being in the range of approximately 0.014 to 0.022 inches, the inner diameter of lumen 202, as indicated by arrows 216, is typically less than approximately 0.008 inches and the thickness of wall 214, indicated by arrows 218, is typically less than approximately 0.005 inches. In one embodiment of a multi-durometer catheter 200 having such dimensions, the thickness of the inner layer of harder material 204, indicated by arrows 220, is less than approximately 0.002 inches. Thus, in this embodiment the thickness of the outer layer of softer material 206, indicated by arrows 222, is approximately less than 0.003 inches.

The type of satisfactory harder material 204 and softer material 206 which can be employed to fabricate catheter 200 vary depending the particular implementation and application of the PTC. In one embodiment, the inner layer of harder material 204 comprises 72 D urethane with the outer layer of softer material 206 comprising 80 A utethane. With this embodiment of a 5 cm long multi-durometer catheter 200, having the above dimensions, for a hydrated catheter at 37° C., the drop in frequency response is only approximately 1 dB at 100 Hz. In some applications, there can possibly be delamination between the two durometers of urethane represented by inner layer of harder material 204 and outer layer of softer material 206. This delamination problem is solved by creating a chemical bond between inner layer of harder material 204 and outer layer of softer material 206 during a real co-extrusion.

Multi-durometer catheter 200 is inexpensive and easy to fabricate using a true co-extrusion technique or by extruding the outer layer over the inner layer by making a second pass through the extruder. The true co-extrusion technique typically obtains a gradient transition between the inner layer and outer layer and the two pass extrusion technique typically obtains a sharp transition between the inner layer and outer layer.

The multi-durometer catheter 200 according to the present invention provides a means of producing a good frequency response in a thin-walled, very small-diameter catheter while maintaining excellent flexibility. The compliance of catheter 200 is primarily derived by the properties of the harder material 204 to produce sufficient frequency response. Nevertheless, the layer of softer material 206 makes catheter 200 kink resistant and flexible. Thus, catheter 200 is easily handled and kink resistant during surgery. In applications where a flexible catheter 200 is not required, a rigid multi-durometer catheter 200 still provides better frequency response than conventional rigid single-durometer catheters.

In one embodiment of multi-durometer catheter 200, inner layer of harder material 204 includes a radiopaque material. For example, in one embodiment, the inner layer of harder material 204 includes an approximately 20-30% barium filled 72 D urethane. One problem with introducing a radiopaque material into a single-durometer catheter is that radiopaque materials are often thrombogenic. This problem is solved with this embodiment of multi-durometer catheter 200, because outer layer of softer material 206 comprises only non-thrombogenic material. In this way, this embodiment of multi-durometer catheter 200 is radiopaque and non-thrombogenic. Alternatively, a softer inner layer having a radiopaque material could be disposed between the inner layer of harder material 204 and the outer layer of softer material 206.

One alternative embodiment of a multi-durometer catheter according to the present invention comprises an outer layer of harder material and an inner layer of softer material. In this alternative embodiment, the compliance of the multi-durometer catheter is still primarily derived by the properties of the harder material to produce sufficient frequency response and the layer of softer material makes the catheter kink resistant.

Example Applications of the Pressure Measurement Device According to the Present Invention The pressure measurement device can be advantageously used to obtain pressures in animals and humans for all of the example uses disclosed in the Brockway et al. '191 patent, such as: for measuring blood pressure in an artery of an animal; for measuring intrapleural pressure in animals; and for measuring intracranial pressure in animals. However, the following three example applications of the pressure measurement device of the present invention illustrate three particularly useful applications, which take advantage of the features of the present invention, such as having a reduced length PTC 22, having a separate PTC 22 and connecting catheter 36, and having the transducer 30 being remote from transmitter housing 44.

Application of Pressure Measurement Device for Measuring Venous Pressure

Figure 6:
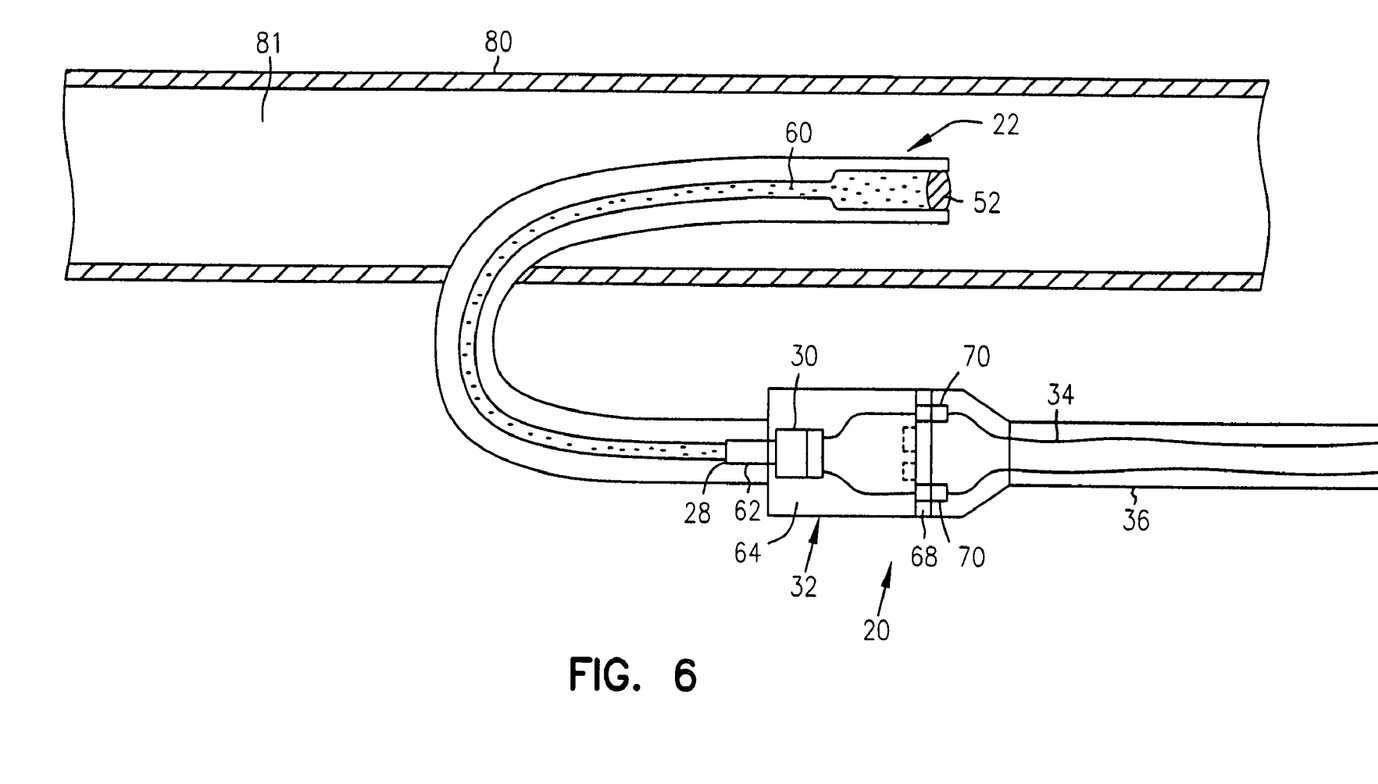
FIG. 6 is a diagram illustrating the application of the pressure measurement device of FIG. 1 to measure venous pressure.

FIG. 6 illustrates an embodiment of the pressure measurement device 20 according to the present invention for measuring venous pressure, such as venous pressure in a laboratory rat. Venous pressure is relatively low and head pressure error can thus be significant and highly undesirable. In this embodiment, the length of PTC 22 (indicated by arrows 50 in FIG. 1) is typically approximately 4 centimeters long and the length of connecting catheter 36 (indicated by arrows 48 in FIG. 1) is typically approximately 25 centimeters long. In this application, PTC 22 typically comprises an approximately 2-3 mm long gel plug 52 at the distal tip 24, with the remainder of PTC 22 filled with low-viscosity fluid 60.

To surgically implant a pressure measurement device according to the present invention in a vein of a rat or other laboratory animal, a vein 80 is exposed, such as an abdominal vein. PTC 22 is inserted into vein 80 to sense pressure of blood 81 and is secured at a point where PTC 22 exits vein 80 using medical grade tissue adhesive or a purse-string suture. As illustrated in FIG. 6, about one-half of the approximately 4 centimeter long PTC 22 is inserted into vein 80. Transducer housing 32 containing transducer 30 is disposed outside of vein 80 and is secured to tissues at a point immediately adjacent to vein 80 and as near to distal tip 24 of PTC 22 as possible. Transmitter 40 is secured to a muscle or within a subcutaneous pocket at a site which is convenient to the surgeon performing the procedure. For example, when PTC 22 is inserted into the abdominal vein of a laboratory rat, transducer housing 32 is typically sutured to the muscle next to the abdominal vein. In this application, transmitter housing 44 is typically sutured to a ventral abdominal muscle at the incision made to access the abdomen.

Application of Pressure Measurement Device for Monitoring Pulmonary Pressure

Figure 7:
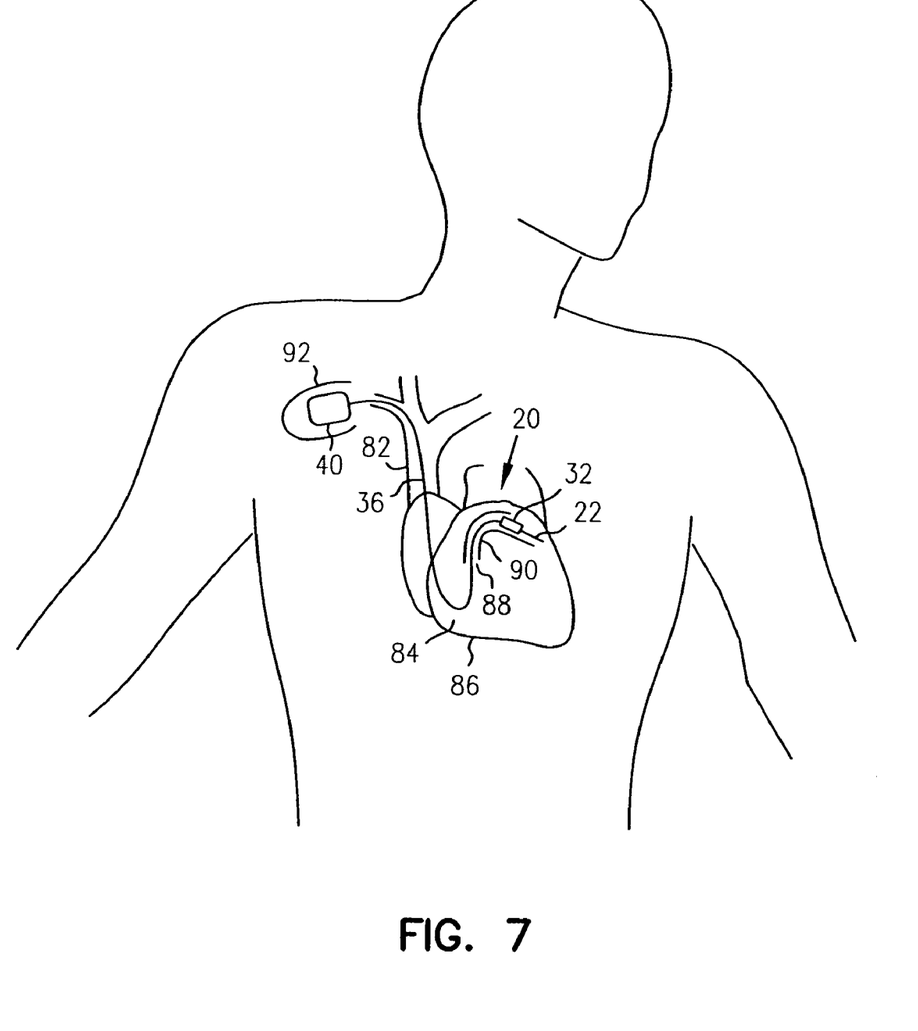
FIG. 7 is a diagram illustrating the application of the pressure measurement device of FIG. 1 to monitor pulmonary pressure.

FIG. 7 illustrates an embodiment of the pressure measurement device 20 according to the present invention employed to monitor pulmonary pressure in a human. In this embodiment, PTC 22 is typically approximately 1-2 cm long and connecting catheter 36 is typically approximately 50 cm long. In this application, connecting catheter 36 must be quite long (e.g., approximately 50 cm). Since the monitored pulmonary pressure is low, head pressure artifact is a problem overcome by using the short PTC 22 (e.g., approximately 1-2 cm). In this application PTC 22 typically contains both viscous gel membrane 52 and low-viscosity fluid 60. Nevertheless, in this application, PTC 22 can be completely filled with viscous gel 52, such as illustrated in FIG. 2B, and still perform acceptably, because of the very short length of PTC 22. In addition, depending on the thermal characteristics of PTC 22, transducer 30, and low-viscosity fluid 60, this application optionally employs a PTC 22 without a larger diameter thin-walled section 54, such as illustrated in FIG. 2C.

To surgically implant the pressure measurement device 20 according to the present invention in this application, PTC 22, transducer housing 32, and connecting catheter 36 are inserted into subclavian vein 82, passed into right ventricle 84 of heart 86, and guided out of heart 86 through pulmonary semilunar valve 88 into pulmonary artery 90. Following the above procedure to position PTC 22 and connecting catheter 36, transmitter housing 44 is disposed in a subcutaneous pocket 92 near the site of entry to subclavian vein 82. As illustrated in FIG. 7, in this application of the pressure measurement device 20 according to the present invention, the complete length of PTC 22 and a large portion of connecting catheter 36 reside within the circulatory system.

Application of Pressure Measurement Device for Monitoring Intracranial Pressure

Figure 8:
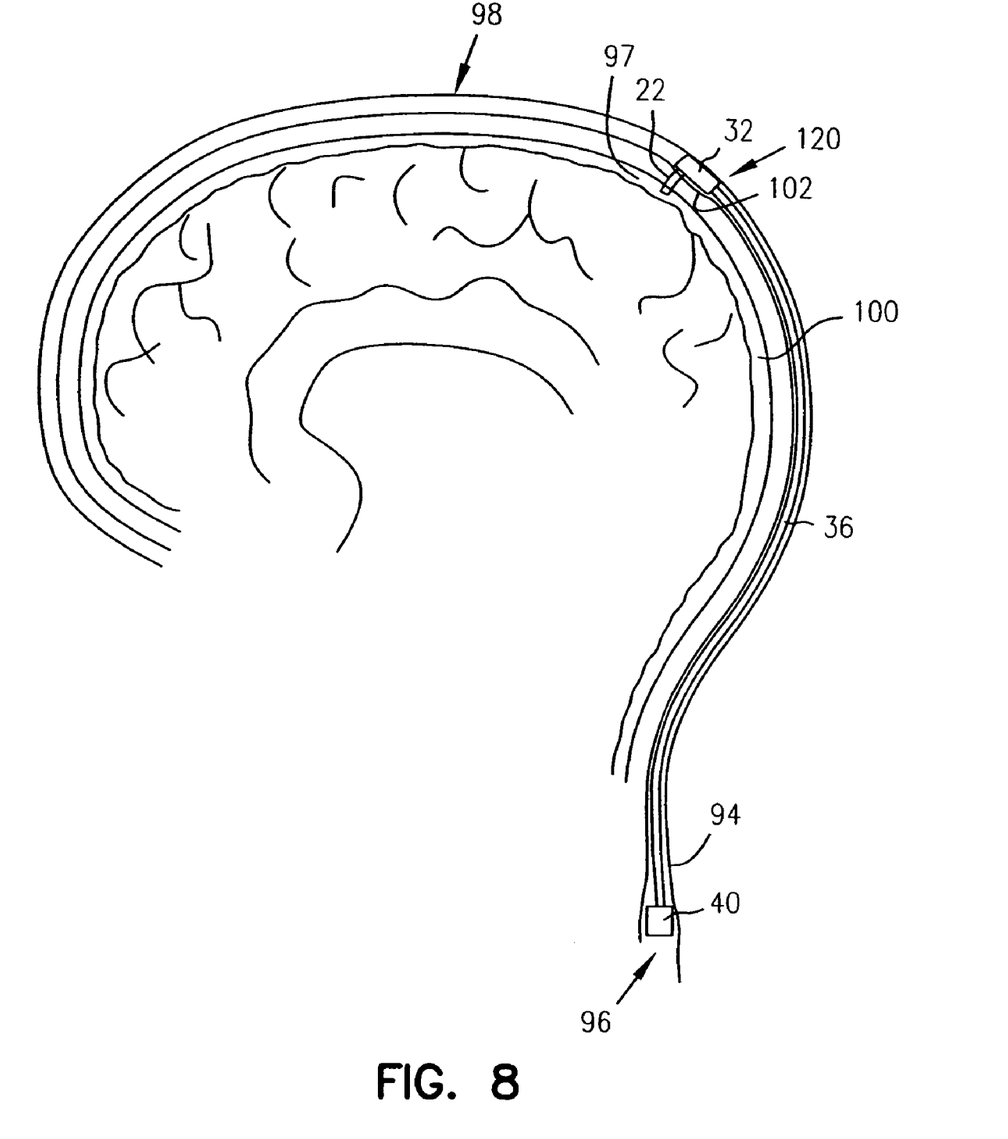
FIG. 8 is a diagram illustrating the application of the pressure measurement device of FIG. 4 to monitor intracranial pressure.

An embodiment of the pressure measurement device 120 according to the present invention for monitoring intracranial pressure is illustrated in FIG. 8. Intracranial pressures are relatively low and thus head pressure errors can be significant. In this application, it is typically undesirable for transmitter housing 44 to be placed beneath the scalp because it may be uncomfortable due to its size. Therefore, transmitter housing 44 containing transmitter 40 is typically placed subcutaneously, as indicated at 94, in a convenient location on the neck of the patient or on the upper ventral thorax, based on surgeons preference. PTC 22 is typically approximately 1.5 cm long and preferably exits transducer housing 32 at an approximately 90 angle. Thus, the right angle pressure measurement device 120 illustrated in FIG. 4 is preferable used in this application. The right angle provides a more convenient surgical placement. In this application, connecting catheter 36 is typically approximately 70 cm long. In this application, PTC 22 typically includes viscous gel membrane 52 at distal tip 24 with the remainder of PTC 22 filled with low-viscoaity fluid 60.

Surgical implantation in this application involves making a subcutaneous pocket 96 at the location 94 where transmitter 40 is to be placed. PTC 22 and connecting catheter 36 are directed under the skin from location 94 to a location 97 within cranium 98 where pressure is to be monitored. Following exposure of cranium 98 at the location 97 where pressure is to be monitored, a hole is drilled through cranium 98. PTC 22 is then directed through the hole into a subarachnoid space 100. To prevent transducer housing 32 from extending above the normal plane of the scalp, a shallow cavity 102 is formed in cranium 98. Transducer housing. 32 is placed in shallow cavity 102. In this embodiment, transducer housing 32 is constructed with a flat profile to inhibit migration under the skin and to improve tolerance by the patient.

Alternative Pressure Measurement Device

Figure 9:
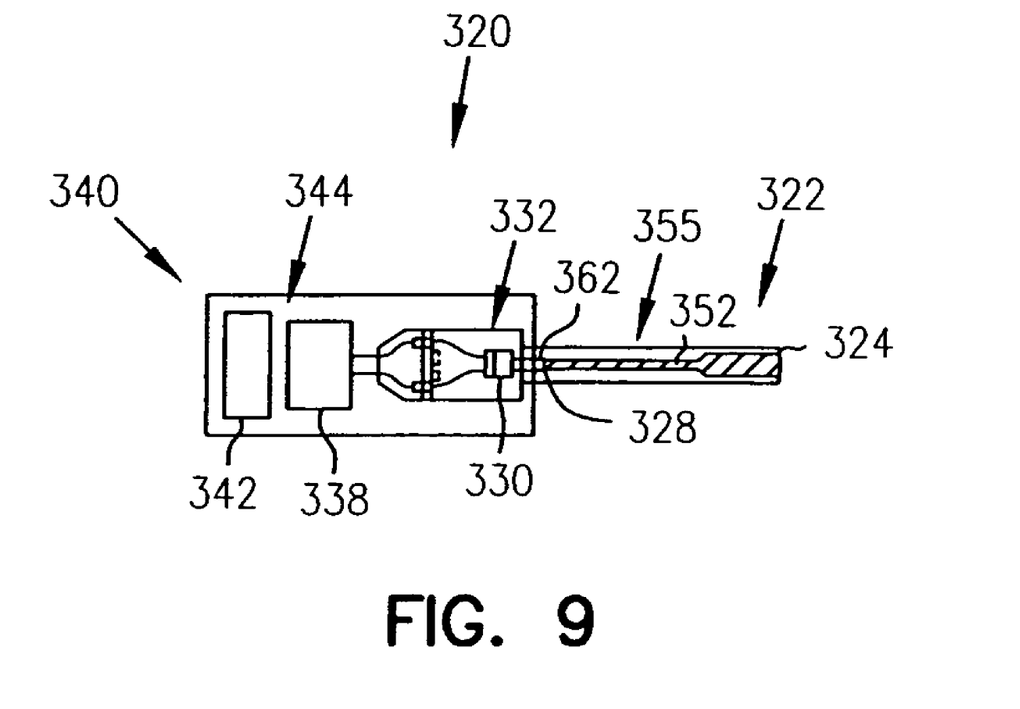
FIG. 9 is a diagram of an alternative pressure measurement device.

An alternative pressure measurement device is illustrated generally at 320 in FIG. 9. Pressure measurement device 320 includes a pressure transmission catheter (PTC) 322 having a distal lumen tip 324 which is positioned within the body of a human or animal at the site where pressure is to be measured. One embodiment of PTC 322 is flexible, while another embodiment of PTC 322 is rigid, and the particular embodiment of PTC 322 selected depends on the given application of pressure measurement device 320. PTC 322 is filled entirely with a pressure-transmitting gel 352 which communicates the pressure at the distal tip 324 of PTC 322 to a proximal lumen end 328 of PTC 322. Thus, a portion of pressure-transmitting gel 352 at distal tip 324 interfaces with the substance in the body area where pressure is to be measured, such as with blood in an artery.

A transducer 330 is in communication with pressure-transmitting gel 352 at the proximal end 328 of PTC 322. As illustrated, PTC 322 is attached to transducer 330 via a nipple 362. Transducer 330 is contained in a transducer housing 332. Transducer 330 responds to variations in the pressure-transmitting gel at proximal end 328 to provide an electrical pressure signal representing variations in the physiological pressure at distal tip 324 on electrical lead wires, which are coupled to an electronics module 338 of a transmitter 340. Electronics module 338 is powered by a battery 342. Battery 342, electronics module 338, and transducer housing 332 are contained within a transmitter housing 344. The electronics module 338 includes signal-processing and telemetry circuitry and a transmitting antenna for generating and transmitting a telemetry signal representing the pressure signal from transducer 330 to an external receiver (not shown) disposed outside of the human or animal. The electrical pressure signal produced by transducer 330 is amplified and filtered with the signal-processing circuitry in electronics module 338 and is then modulated onto a radio-frequency carrier by the telemetry circuitry in electronics module 338 for transmission to the external receiver.

In alternative pressure measurement device 320, the transducer 330 is contained within transmitter housing 344, and PTC 322 is filled entirely with pressure-transmitting gel 352 (i.e., a low viscosity fluid is not used). This embodiment can be employed in applications where PTC 322 is very short and the transmitter housing 344 is sufficiently small to enable it to be located at the pressure source.

Pressure transmitting gel 352 is a biocompatible and blood-compatible gel or other gel-like material that provides a direct interface with the tissue or fluid from which pressure is to be measured, such as blood in an artery. Gel 352 provides a means of retaining fluid within PTC 322 and can be comprised of any material which is capable of flowing as does a viscous fluid and contains intramolecular forces which make it very unlikely that any portion of this material will dissolve, break apart, slough off, or wash away when measuring physiological pressure within a human or animal. Gel 352 must be viscous enough not to wash out of PTC 322, but also must be low enough in viscosity that it can "flow" without significant pressure differential. In one embodiment of the invention, pressure transmitting gel 352 is a silicone gel which contains cross-linked molecular entities.

CONCLUSION

The pressure measurement device according to the present invention can be employed to sense numerous internal body pressures in humans and animals including pulmonary pressure, venous pressure, left ventricle pressure, intracranial pressure, bladder pressure, and other physiological pressures. Pressure information sensed with the pressure measurement device according to the present invention is available for diagnostic purposes, research, or feedback for closed-loop control of infusion pumps capable of administering pharmaceutical agents.

The pressure measurement device according to the present invention, such as pressure measurement device 20, overcomes the above-discussed disadvantages of the previous pressure measurement devices, offers significant new opportunities for more accurate measurement of pressure, and opens new applications for pressure measurement in animals and humans. The pressure measurement device according to the present invention obtains high-fidelity measurements with negligible head pressure error in applications where the distance from the distal tip of the PTC to the transmitter is large.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. An apparatus for measuring physiological pressure comprising:
   a pressure transmission catheter having a lumen filled with a pressure transmitting medium and implantable in an area having a physiological pressure;
   a transducer in communication with the pressure transmitting medium and coupled to an electrical wire for providing a signal representing variations in the physiologic pressure on the electrical wire;
   a connecting catheter carrying the electrical wire to a location remote from the transducer;
   the pressure transmitting catheter comprising an inner layer defining the lumen and an outer layer disposed about the inner layer, wherein:
   the inner layer comprises a first material, and
   the outer layer comprises a second material that is softer than the first material, wherein the pressure transmission catheter has a length short enough to avoid significant head pressure artifact and provide sufficient dynamic response.

2. An apparatus for measuring physiological pressure comprising:
   a pressure transmission catheter having a lumen filled with a pressure transmitting medium and implantable in an area having a physiological pressure;
   a transducer in communication with the pressure transmitting medium and coupled to an electrical wire for providing a signal representing variations in the physiologic pressure on the electrical wire;
   a connecting catheter carrying the electrical wire to a location remote from the transducer;
   the pressure transmitting catheter comprising an inner layer defining the lumen and an outer layer disposed about the inner layer, wherein:
   the inner layer comprises a first material, and
   the outer layer comprises a second material that is softer than the first material, wherein the pressure transmitting medium comprises a slidable plug and a low-viscosity liquid.

3. An apparatus for measuring physiological pressure comprising:
   a pressure transmission catheter having a lumen filled entirely with a pressure transmitting gel and implantable in an area having a physiological pressure; and
   a transducer in communication with the pressure transmitting gel and coupled to an electrical wire to provide a signal on the electrical wire which represents variations in the physiologic pressure;
   the pressure transmitting catheter compromising an inner layer defining the lumen and an outer layer disposed about the inner layer, wherein:
   the inner layer comprises a first material having a first hardness,
   the outer layer comprises a second material having a second hardness, and the first hardness is greater than the second hardness, wherein the electrical wire is carried within a connecting catheter carrying the electrical wire to a location remote from the transducer wherein the pressure transmission catheter has a length short enough to avoid significant head pressure artifact and provide sufficient dynamic response.

4. An apparatus for measuring physiological pressure comprising:
   a pressure transmission catheter having a lumen filled entirely with a pressure transmitting gel and implantable in an area having a physiological pressure; and
   a transducer in communication with the pressure transmitting gel and coupled to an electrical wire to provide a signal on the electrical wire which represents variations in the physiologic pressure;
   the pressure transmitting catheter compromising an inner layer defining the lumen and an outer layer disposed about the inner layer, wherein:
   the inner layer comprises a first material having a first hardness,
   the outer layer comprises a second material having a second hardness, and the first hardness is greater than the second hardness, wherein the electrical wire is carried within a connecting catheter carrying the electrical wire to a location remote from the transducer wherein the pressure transmission catheter has a length in the range from approximately two millimeters to approximately four centimeters.

* * * * *

UNITED STATES PATENT AND TRADEMARK OFFICE
CERTIFICATE OF CORRECTION

PATENT NO. : 7,347,822 B2  Page 1 of 1
APPLICATION NO. : 11/304452
DATED : March 25, 2008
INVENTOR(S) : Brian P. Brockway et al.

It is certified that error appears in the above-identified patent and that said Letters Patent is hereby corrected as shown below:

Column 16, line 21 (claim 3), after "transducer" insert --,--.

Column 16, line 45 (claim 4), after "transducer" insert --,--.

Signed and Sealed this

Thirtieth Day of June, 2009

JOHN DOLL
*Acting Director of the United States Patent and Trademark Office*